(12) United States Patent
Scorvo

(10) Patent No.: US 6,969,365 B2
(45) Date of Patent: Nov. 29, 2005

(54) ADJUSTABLE ORTHOTIC BRACE

(76) Inventor: Sean K. Scorvo, 1964 NW. Iowa Ave., Bend, OR (US) 97701

(*) Notice: Subject to any disclaimer, the term of this patent is extended or adjusted under 35 U.S.C. 154(b) by 124 days.

(21) Appl. No.: 10/418,508

(22) Filed: Apr. 16, 2003

(65) Prior Publication Data

US 2003/0212356 A1    Nov. 13, 2003

Related U.S. Application Data

(60) Provisional application No. 60/387,030, filed on Jun. 4, 2002, provisional application No. 60/373,368, filed on Apr. 16, 2002.

(51) Int. Cl.[7] ............................................... A61F 5/00
(52) U.S. Cl. ........................... 602/16; 602/20; 602/26; 602/27
(58) Field of Search ............................. 602/16, 20, 26, 602/27

(56) References Cited

U.S. PATENT DOCUMENTS

| | | |
|---|---|---|
| 5,052,379 A | 10/1991 | Airy et al. |
| 5,462,517 A | 10/1995 | Mann |
| 5,472,410 A | 12/1995 | Hamersly |
| 5,472,413 A | 12/1995 | Detty |
| 5,954,621 A | 9/1999 | Joutras et al. |
| 6,290,664 B1 | 9/2001 | Nauert |
| 6,312,398 B1 | 11/2001 | Cencer |
| 6,328,706 B1 | 12/2001 | Yattavong |
| 6,336,909 B2 | 1/2002 | Gildersleeve et al. |
| 2001/0036790 A1 | 11/2001 | Kornbluh et al. |

OTHER PUBLICATIONS

M.Shahinpoor, Y. Bar-Cohen, T.Xue, J.O. Sipson and J. Smith; *Ionic Polymer-Metal Composites (IPMC) As Biomimetic Sensors and Actuators*, SPIE's 5th Annual International Symposium on Smart Structures and Materials, Mar. 1-5, 1998, San Diego, CA, Paper No. 3324*27, pp. 1-17.
Mohsen Shahinpoor and Kwang J. Kim; Institute of Physics Publishing, Smart Materials and Structures, Oct. 2001, pp. 819-833.

*Primary Examiner*—Henry Bennett
*Assistant Examiner*—Dinnatia Doster-Greene
(74) *Attorney, Agent, or Firm*—Chernoff, Vilhauer, McClung & Stenzel

(57) ABSTRACT

An orthotic brace is adjustable in response to a sensed brace parameter or a treatment regimen to optimize the attachment of the brace to a limb and alter the support provided to the muscles and ligaments of the joint.

21 Claims, 11 Drawing Sheets

ADJUSTABLE ORTHOTIC BRACE

CROSS-REFERENCE TO RELATED APPLICATIONS

This application claims the benefit of 60/387,030 filed Jun. 4, 2002 and the benefit of 60/373,368 filed Apr. 16, 2002.

BACKGROUND OF THE INVENTION

The present invention relates to an orthotic brace for an anatomic join and, more particularly, to an adjustable orthotic bracing system.

An orthotic brace is used to counteract instability in a joint which is typically related to a soft tissue injury or joint deformity. Braces stabilize the joint area and limit joint movement to a defined range of motion, protecting the joint and the natural muscular and ligamentous joint stabilizers. A brace can also be used to prevent injury resulting from excessive motion or force by restricting flexion, extension, rotation, or lateral movement of the articulating joint. Braces are often used to protect joints during certain activities, such as athletics, or as part of physical therapy or a strength augmentation program following an injury or surgery. Ideally, a brace synergistically aids the inherent muscular and ligamentous joint stabilizers throughout a range of motion in resisting rotation and translation forces that might injure the joint. The ideal brace permits a full range of prescribed joint motion while preventing excessive displacement or force that might injure the joint and protects other parts of the limb, the user's body, and other persons from injury as a result of coming in contact with the brace.

Several types of brace devices are available. A sleeve is an expandable, slip-on device that typically comprises nylon-covered neoprene. Sleeves are simple, easy to fit and relatively inexpensive. Sleeves compress the area around the joint and increase the temperature at the joint. The increased compression and temperature may be a basis of perceived benefits reported by patients, but a simple sleeve does not apply leverage to the joint which is necessary for ligamentous support and lessening the likelihood of joint injury.

The leverage necessary to limit joint motion and loading is typically provided by one or more sets of articulated bars of a bracing element that are secured to the limb on opposing sides of the joint. Typically, the hinged bars are bound to the soft tissue of the limb by releasable bindings, an elastic sleeve or other similar attaching element. The pivot axis of the hinge of the articulated bracing element is generally aligned with the pivot axis of the joint so that the joint can move through a range of planar motion defined by the articulation of the hinged bars. The hinge of the articulated bracing element commonly includes adjustable stops so that the motion of the bracing element and the corresponding flexing of the joint can be limited.

In addition, a brace may be used to treat flexion or extension contractures that prevent the joint from being fully extended or fully flexed, respectively. Contractures and joint stiffness are typically the result of disuse of the joint following injury or surgery. Typically, contractures are treated with physical therapy including flexing of the joint against a resistance or weight. Spring-biased splints or braces providing a force to either resist or urge joint motion are commonly used to treat contractures. Hamersly, U.S. Pat. No. 5,472,410 discloses a brace that can apply a force resisting joint flexing.

Braces are also employed to control compartmental loading or the relative loading on the medial and lateral sides of a joint. The bars of the articulated brace element comprise a lever system controlling lateral displacement of the limb elements on opposing sides of the joint and, therefore, the compartmental loading of the joint. Typically, each of the bars of the bracing element is bound to the appropriate limb element at, at least, two spaced apart locations. The distal and the hinged proximal ends of the bars serve as fulcrums of the levers and the tensioning structures, the limb attaching elements proximal to the joint, are used to apply a reaction force substantially normal to the limb. This force pulls the joint toward the bracing element altering the relative portions of the joint load borne by the medial and lateral sides of the joint. Gildersleeve, U.S. Pat. No. 6,336,909 B2 discloses a brace for medial/lateral joint loading that includes a bracing element that can be semi-permanently deformed to alter compartmental loading and to customize the brace for a particular limb or treatment regimen.

While the ideal brace would limit joint motion to a prescribed range and support the natural muscular and ligimentous support structure of the joint throughout the range of motion, the control of the joint provided by a brace is limited substantially by the connection of the brace to the soft tissue of the limb. As the limb is flexed, the skin and muscle around the joint stretch and move producing large translations of the tissue to which the brace is attached. The thickening and thinning of muscle groups during joint flexing causes the positions of the bones inside the muscle mass and the shape and size of the limb at the points of attachment to change to substantially during joint movement.

The protection and efficacy of treatment provided by an orthotic brace are limited by the inability of braces to accommodate the changes in the limb resulting from joint operation. Even a custom fitted brace does not optimally control a joint throughout the range of motion. What is desired therefore, is an orthotic brace that is adjustable to respond to external influences acting on the joint, accommodate changes in the user's body resulting from limb motion, and enhance the effects of a treatment regimen.

DETAILED DESCRIPTION OF THE INVENTION

Figure 1:
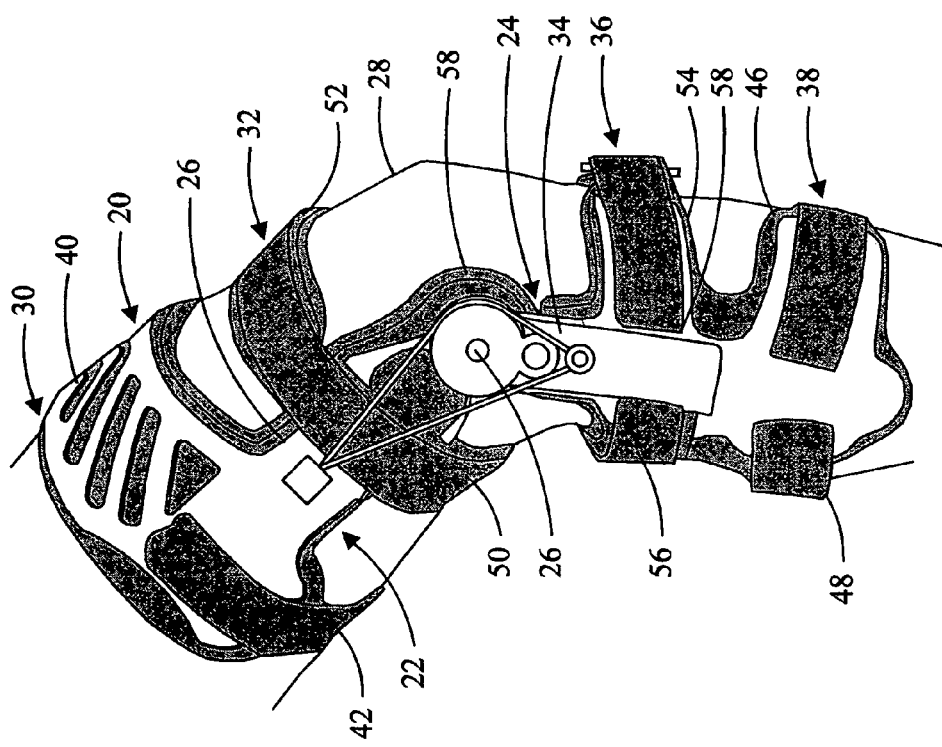
FIG. 1 is a side view of an adjustable ORTHOTIC brace.
Figure 2:
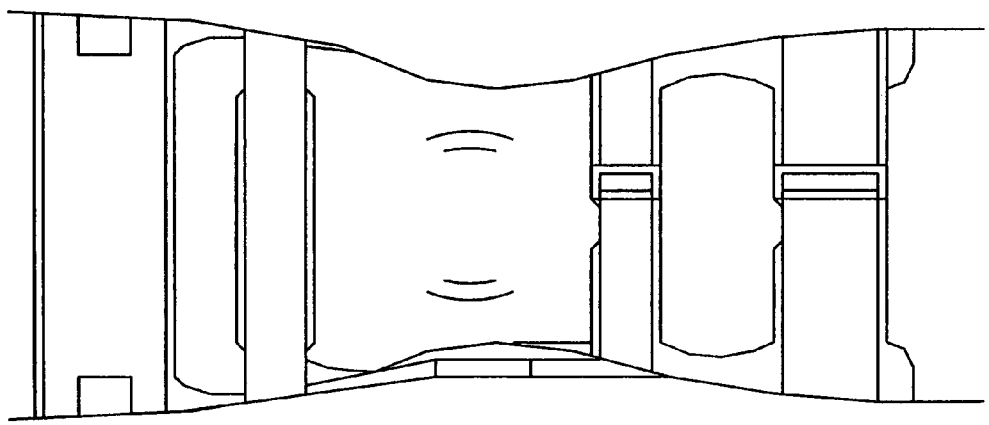
FIG. 2 is frontal view of an adjustable orthotic brace.

A typical orthotic brace comprises generally a joint stabilizing bracing element and a plurality of attaching elements to bind the bracing element to the soft tissue of the limb elements, above and below a joint. FIGS. 1 and 2 illustrate an exemplary orthotic knee brace 20. The bracing element comprises generally of a pair of levers including bars connected by a hinge structure. Thus, the exemplary knee brace 20 includes a femur lever, generally designated, 22 and a tibia lever, generally designated, 24. The levers 22 and 24 are operatively connected at the lateral side of the leg proximate the knee by a hinge structure 26. The hinge structure permits the distal ends of the femur lever 22 and the tibia lever 24 to be displaced relative to each other as the joint is flexed. The movement of the distal ends of the levers of an orthotic brace is substantially relative rotation in a plane, however, monocentric, bicentric, and polycentric hinges are utilized in orthotic braces to more precisely conform the lever displacement to the often complex articulation of specific joints.

The femur lever 22 comprises a generally elongated, flat femoral side bar 26 that extends generally longitudinally along the lateral or outer side of the thigh 28 and a plurality of spaced apart femoral side bar attaching elements 30 and 32. Similarly, the tibia lever 24 comprises an elongated, flat tibial side bar 34 located generally longitudinally along the lateral or outer side of the calf and a plurality of spaced apart tibial side bar attaching elements 36 and 38. The levers of some braces for the knee, elbow, and other joints include pairs of hinged bars, typically arranged generally longitudinally along opposite sides of the limb, these being a lateral or outer side bar and a substantially similar medial or inner side bar on the inside of the limb.

The exemplary knee brace 20 is attached to the limb elements, the femur, above the knee, and the tibia, below the knee, by a plurality of attaching elements that constrain the levers to the soft tissue of the limb elements. The femoral side bar 26 is bound to the femur at its distal end by a first attaching element, an upper thigh cuff 30, that servers as a fulcrum for the femur lever. The upper thigh cuff 30 of the brace 20 comprises a cuff base 40 that is rigidly attached to the femoral side bar 26 and an upper thigh binding 42 having ends operatively connected to the cuff base. The upper thigh binding 42 is wrapped around the thigh and constrains the cuff base and femur lever 22 to the thigh. Similarly, another attaching element, the lower calf cuff 38, comprising a cuff base 46 and a lower calf binding 48 serves as the fulcrum of the tibia lever 24.

The upper thigh cuff base 40 is preferably substantially rigid and often formably adjustable to accommodate thighs of differing curvatures. A substantially rigid but formably adjustable upper thigh cuff base 40 can be fashioned from a metal core, preferably of aluminum, laminated on both sides with a covering, typically plastic, to protect the wearer and others from sharp edges or corners and improve wearer comfort.

The lower calf cuff base 46 typically comprises a flexible plastic, such as polyethylene. A flexible lower calf cuff base 46 is generally desirable to accommodate a variety of calf girths and permit adjustment of the tibial side bar 34 to prevent twisting relative to the hinge 26 which might otherwise be caused by calves that are undersized or oversized for the lower calf cuff base.

The attaching element of the femur lever 22 adapted to apply a reaction force to the femur proximal the knee joint is an adjustable lower thigh tensioning structure 32. Likewise, an upper tibial tensioning structure 36 applies the reaction force to the tibia proximal the knee joint. The lower thigh tensioning structure 32 and the upper tibial tensioning structure 36 of many braces comprise a binding that passes around the leg and the bracing element to bind the bracing element to the limb element. In the exemplary brace 20, the lower thigh tensioning structure 32 comprises a fabric binding 50 wrapped around the leg and the outer side of the bracing element 22. An anterior thigh pad 52, held in position by the binding 50, spreads the load produced by the binding over a greater area the soft tissue of the thigh.

The upper tibial tensioning structure 36 is similar in construction to the lower tibial cuff 38 and comprises a flexible plastic cuff base 54 affixed to the tibial lever 34 and extending across the anterior of the tibia. The tensioning structure 36 includes a fabric binding 56 that passes through elongated eyelets 58 in the plastic cuff base 34.

Lateral force can be applied to the knee by tensioning the bindings 50 and 56 of the lower thigh tensioning structure 32 and the upper tibial tensioning structure 36. Tension in the bindings pulls the distal ends of the femur and the tibia, respectively, toward the bracing element 22 and applies a positive differential force couple to the femur and tibia proximal the knee joint. By adjusting the tension in the bindings of the tensioning structures, the compartmental loading or the relative portions of the load on the joint supported by the medial and lateral sides of the joint can be varied to protect compartments of the joint and treat certain joint conditions. A condyle pad may be placed between the hinge and the knee to bear against the side of the knee to control lateral knee instability. The surfaces of the brace in contact with the wearer are commonly covered by a fabric surfaced foam material 58 for wearer comfort and protection. A flexible, fabric sheath (not illustrated) may also be worn between the brace and the skin to reduce chaffing and help stabilize the brace.

The thigh and tibial cuffs and tensioning structures of the exemplary brace 20 utilize flexible, fabric-like bindings to bind the bracing element 22 to the soft tissue of the limb. The bindings of the exemplary brace typically include a short length of a hook material on one side of the binding proximate to at least one end of the binding. A complementary eye material is attached to another portion of the binding. The binding is wrapped around the limb and the end of the binding is doubled over the eye material to secure the end of the binding as required. While the cuffs and tensioning structures of the exemplary brace 20 include formed cuff bases and fabric bindings with hook and eye fastening elements, other attaching elements and methods, such as elastic sleeves and straps with buckles, may be used to constrain an orthotic brace and a limb.

The major factor limiting the ability of an external device, such as the orthotic brace 20, to control a joint is deflection of the soft tissue to which the brace is bound by its attaching cuffs and tensioning structures. The skin, fatty tissue, and muscles, particularly when flaccid, are easily rolled around the limb. In addition, the soft tissue translates longitudinally on the limb in response to the application of force. This is partly due to the thickening and thinning of the muscles as they flex to operate the joint. Further, soft tissue compresses in response to pressure from the brace cuffs and bindings. In addition, the dimensions of the limb change substantially as the muscles flex to operate the joint causing the tension exerted at the cuffs and tensioning structures to increase and decrease as the joint is flexed. The effects of soft tissue deflection vary with body type, muscle tone, and limb element position during movement. Maximizing the cuff and strap areas bearing on the soft tissue and increasing the separation of the attaching elements reduce the pressure acting on the soft tissue and improve joint control, but limb size limits the dimensions of the brace and soft tissue movement cannot be eliminated. Simply tightening the bindings of a brace does not eliminate the effects of soft tissue compression, translation, and rotation, and the binding tension is limited by user comfort and adverse effects on circulation.

Lateral force can be applied to the joint by increasing the tension in the straps of the tensioning structures. As the joint is pulled toward or permitted to move away from the bracing element, the load on the joint can be shifted from one side of the joint to the other. Such compartmental loading of a joint may be desired as part of a treatment regime or to protect a specific element of the joint structure. For example, as the knee is pulled toward bracing element 22, by increasing the tension in the binding of the lower thigh tensioning structure 32 and the upper tibial tensioning structure 36, the portion of the load on the knee that is borne by the side of the joint opposite the bracing element is increased and the portion of the load on the side of the joint nearest the bracing element is reduced. Conversely, the load on the side of the joint opposite the bracing element can be reduced or unloaded and the loading of the side of the joint adjacent to the bracing element increased or loaded by reducing tension in the bindings of the tensioning structures and permitting the joint to move away from the bracing element.

The effect or result of changing the tension in the bindings of the tensioning structures is to apply leverage to the proximal and distal portions of the respective limb elements and to displace the joint laterally relative to the hinged bracing element 22. The resultant compartmental loading is determined by the force exerted by the tensioning structures and by the relative profiles of bracing element and the surface of the limb against which the bracing element bears. Since the profile of the surface of the limb varies between users, bracing elements are often purposefully and semi-permanently deformed in a direction substantially normal to the limb to provide a custom profile that will properly load the joint when force is applied by the tensioning structures. However, semipermanent deformation of the brace cannot accommodate the changing shape of the muscles as the joint is flexed and may cause undesirable loading of the joint during certain portions of the joint's range of motion. Further, altering the shape or deflection characteristics of the bracing element in response to a dynamic condition, such as a blow to the side of the leg, particularly when the tibia and femur are in a vulnerable alignment, may provide added protection for the joint.

Orthotic braces are also used to assist or resist flexion or extension of the joint as part of physical therapy or strength augmentation, particularly during joint rehabilitation. Typically, such a brace includes a spring or similar device to assist or resist the flexing of the hinged bracing element. These devices can often be adjusted to vary the general level of resistance or assistance exerted on the levers of the brace, but the force-joint displacement characteristics are generally a function of the design of the force exerting element and not readily adjustable to permit the force to be varied at specific points in the joint's articulation so that the relationship of force and articulation can be tailored to a treatment regimen.

The present inventor concluded that the performance of an orthotic brace could be improved if the characteristics of the brace could be adjusted dynamically to optimize the attachment of the brace to the joint, optimize the shape of the bracing element, and vary the resistance or assistance to joint articulation in response to changes in the limb or events effecting the limb or to accomplish a particular function or treatment regimen. The preferred materials for use in such a brace include, for example, piezoelectrics, electroactive polymers, or a combination thereof.

One of the many features of the present invention is the use of active, dynamic materials to assist in achieving the desired effect. The result is likewise unique in that the one of the goals is to actively reduce injury or rehabilitate a previous injury. Previously existing devices espousing the same goal, generally achieved their ends by physically limiting the joint's movements in a range of motion, instead of permitting generally normal movement up to a point, but then counteracting injury causing extremes in joint motion.

Dynamic materials include but are not limited to electroactive polymers and piezoelectric compounds. Unlike a traditional electric motor, these materials deform to do work directly, creating stress and strain within the material itself, and affecting the surrounding environment via application of the stress and/or strain. This is a conceptual shift given that the material itself does some work, as opposed to necessitating merely a mechanical linkage to a traditional electric motor. The use of the materials also gives significant advantages in weight reduction, conformability, deformability, and reaction speed to a detected force.

It is noted that the terms electractive, polymer, piezoelectric material, electrostrictive, magnetostrictive material may be used interchangeably to describe the aforementioned dynamic materials. However, it is noted that these descriptions are not exclusive. In addition, these descriptions may likewise be further subdivided into various categories. Electroactive polymers/electrostrictive materials, for example, may be subdivided into three types: 1) electronic (driven by electric forces involving the movement of electrons), 2) ionic (consisting of electrodes and elcetrolytes and involving the movement of anions/cations), and 3) molecular (exemplified by, but not limited to, carbon nanotubes).

Figure 3:
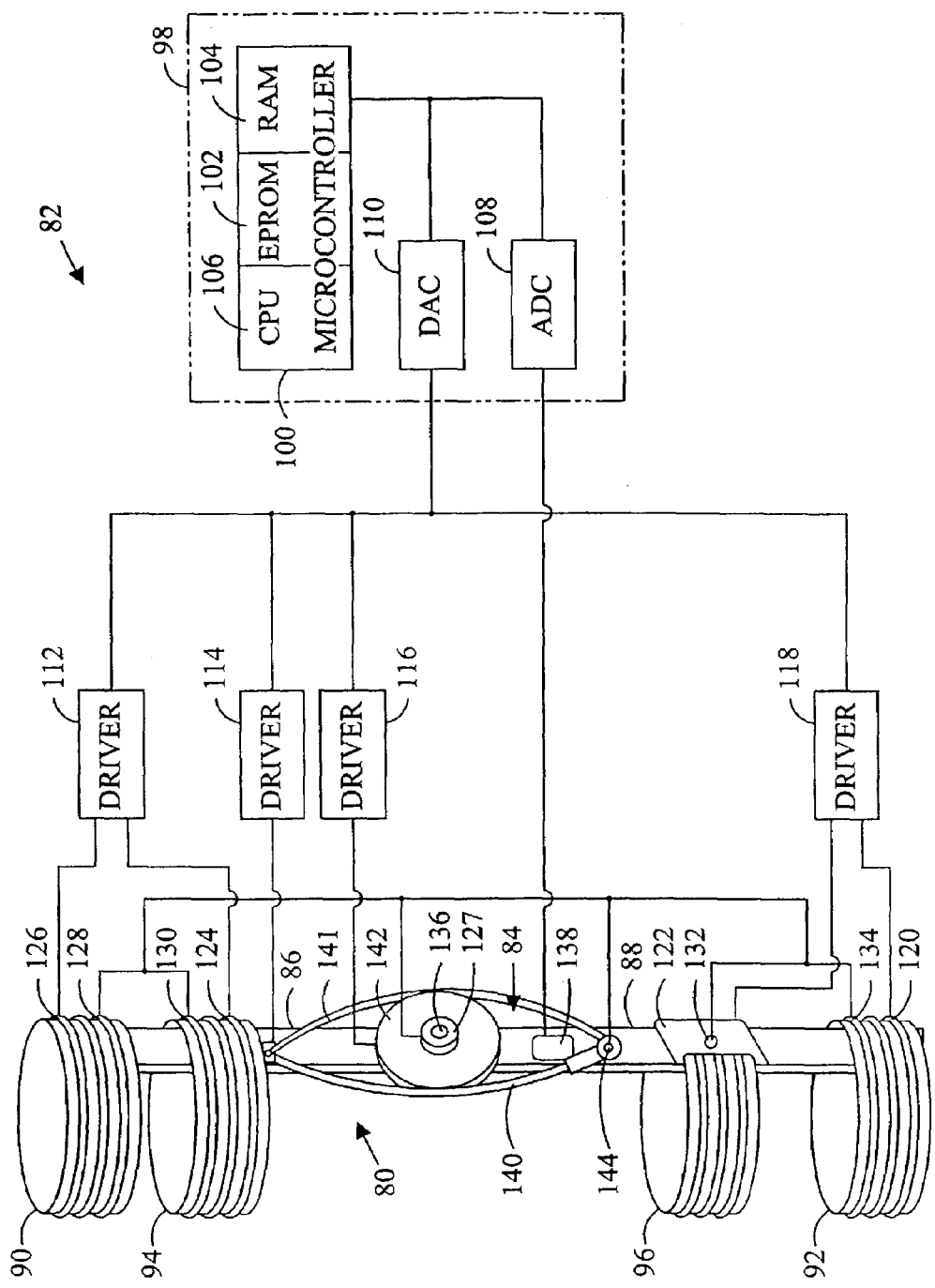
FIG. 3 is a block schematic of an adjustable orthotic bracing system.

The brace 80 is an example of such an adjustable orthotic brace and comprises an element of a dynamically variable brace system 82 illustrated schematically in FIG. 3. While the brace 80 is a brace of the type generally suitable for application to a knee, the brace is an example of an adjustable orthotic brace and similar principles may be applied to braces for other joints. Generally, the brace system 82 comprises a bracing element 84 including hinged first 86 and second 88 levers, a plurality of brace attaching elements (e.g., upper and lower cuffs 90 and 92, respectively, and tensioning structures 94 and 96), one or more sensing transducers sensing brace parameters, one or more loading transducers to apply force or displacement to the various elements of the brace to vary the characteristics of the brace, and a controller 98 to generate appropriate signals to the loading transducers to alter the brace according to a treatment regimen or in response to a change in a brace parameter sensed by a sensing transducer. In the brace system 82, the controller comprises generally, a microcontroller 100 including an erasable, programable, read-only memory (EPROM) 102 to store program instructions used to relate brace parameters, including requirements of a treatment regimen and sensed brace parameters, to output signals directing the loading transducers to alter a load applied to or displacement of one or more elements of the brace 80; random access memory (RAM) 104 to store data and program instructions during processing; and a central processor (CPU) 106 to execute the program instructions and output signals directing action by the loading transducers. The controller 98 typically includes an analog-to-digital convertor (ADC) 108 to convert analog signals output by the sensing transducers to digital data suitable for use by the microcontroller 100, and a digital-to-analog convertor (DAC) 110 to convert the digital output of the microcontroller 100 to analog signals for operating one or more drivers 112, 114, 116, and 118 operating the loading transducers.

The brace 80 includes a plurality of sensing and loading transducers to sense bracing parameters and alter one or more characteristics of the brace. The brace 80 includes sensing transducers to measure forces exerted by the attaching elements, including upper 90 and lower 92 cuffs and upper 94 and lower 96 tensioning structures; the angular displacement of the upper 86 and lower 88 levers of the bracing element 84, and stress in and displacement of the levers 86 and 88. In addition, the brace includes a plurality of loading transducers to apply force assisting or resisting pivoting of the upper 86 and lower 88 levers, deflect the bracing element 84 substantially normal to the limb to alter compartmental loading of the joint, and to alter force exerted by the attaching elements 90, 92, 94, and 96 in binding the bracing element to the limb. As a result, the brace system can dynamically alter the characteristics of the brace 80 to respond to changes in the soft tissue supporting the brace, alter compartmental joint loading, and vary the resistance to joint flexion and extension as a function of, at least, a predefined treatment regimen, joint position, soft tissue conditions, and limb shape. While examples of specific transducer and transducer technologies are specifically described herein, there are a number of other known transducers that can be used to perform the various functions.

Figure 4:
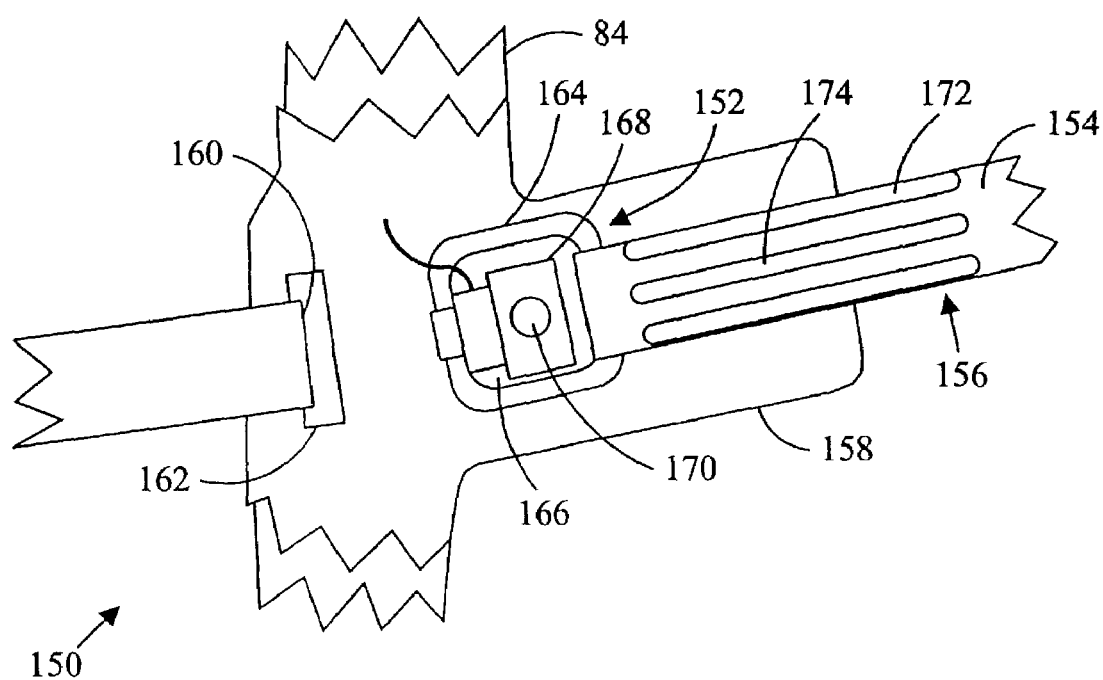
FIG. 4 is plan view of a portion of an attaching element for an orthotic brace.

The effectiveness of the brace in controlling the joint is limited by the performance of the elements that bind the brace to the soft tissue of the limb. While displacement of soft tissue cannot be prevented, the exemplary adjustable brace 80 includes sensing transducers 128, 130, 132 and 134 to sense parameters related to the interface of the soft tissue and the attaching elements and loading transducers 120, 122, 124, and 126 to adjust the attaching elements according to a treatment regimen or the changing characteristics of the interface between the brace and the soft tissue. For example, as the joint is flexed, the dimension and tone of the muscles change. As a result, the force binding the limb to the bracing element and the effectiveness of the attaching elements in resisting brace movement and controlling the joint varies. The attaching elements of the adjustable brace 80, the upper thigh 90 and lower tibial 92 cuffs and the tensioning structures 94 and 96, include sensing transducers to detect changes in the tension of the bindings and loading transducers to alter the attaching elements to maintain an optimal restraining force. FIG. 4 illustrates an exemplary attaching element 150 for an adjustable brace that includes an exemplary sensing transducer 152 to detect the tension in a binding 154 and a loading transducer 156 to alter the tension in response to signals from the controller 98. The attaching element 152 includes a cuff base 158 formed from a plastic covering of the bracing element 84 and a binding 154 that encircles the limb and is attached to the cuff base at each end. The binding 152 is attached to the cuff at a first end 160 by passing the binding through an elongated eyelet 162 in the plastic cover, folding the end back onto the binding, and attaching the end to the body of the binding with complementary hook and eye material or a buckle. The second end of the binding 154 is attached to the cuff 158 by passing the end of the binding through a ring 164, folding the end back, and sewing the end to the binding. The sensing transducer 152 comprises an instrumented link that attaches the binding 154 to the cuff 158. The ring 164 bears on an electrostatic polymer transducer or piezoelectric transducer 166 that is attached to a mounting block 168. The mounting block is riveted 170 to the plastic cuff 158. Tension in the binding 154 exerts a force on the ring 164 causing the piezoelectric transducer 166 to be compressed. It is to be understood that alternatively the piezoelectric materials (sensors and/or actuators) may be any suitable material, such as for example, electroactive polymers (e.g., ionic, electronic, and molecular electroactive polymers). Some electroactive polymers include active gels, electrorestrictive polymers, carbon nanotubes, magnetorestrictive polymers, dielectric polymers and elastomers, liquid crystal elastomers, and ionic polymer metal composites.

Piezoelectric and electrostrictive materials develop a polarized electric field when placed under stress or strain. Conversely, they undergo dimensional changes in an applied electric field. The dimensional change (i.e., expansion or contraction) of a piezoelectric or electrostrictive material is a function of the applied electric field. Piezoelectric and electrostrictive materials can possess a large number of combined and useful properties such as piezoelectric (electric field dependent strain), electrostrictive, dielectric, pyroelectric (temperature dependent polarization), ferroelectric (electric field dependent polarization) and electrooptic (electric field dependent optical birefringence). These devices have a wide range of applications which include actuators, sensors, switches, benders, accelerometers, and strain gauges.

Under an applied electric field, a piezoelectric crystal deforms along all its axes. It expands in some directions and contracts in others. The piezoelectric or strain coefficient describing this deformation is commonly denoted by the tensor $d_{ij}$:

$$d_{ij} = X/E_i (\text{constant } X) = P_i/X_j (\text{constant } E)$$

where x equals strain (extension per unit length); X equals stress (force per unit area); E equals electric field (volts per meter), and P equals polarization (Coulombs per square meter). The subscripts i,j refer to the crystal axes, or in the case of ceramics, to the direction of polarization of the ceramic. For example, $d_{31}$ is the strain coefficient in the lateral direction while $d_{33}$ is the strain coefficient for the longitudinal direction.

A typical device such as a direct mode transducer makes direct use of a change in the dimensions of the material, when activated, without amplification of the actual displacement. The direct mode actuator typically includes a piezoelectric or electrostrictive plate sandwiched between a pair of electrodes formed on its major surfaces or embedded within the material. The device is generally formed of a material which has a sufficiently large piezoelectric and/or electrostrictive coefficient to produce the desired strain in the plate. Applying a voltage of appropriate amplitude and polarity between some dimensions of the device, it will cause the piezoelectric (or electrostrictive) material to contract or expand in that direction. On the other hand, applying a load to extend or compress a piezoelectric transducer causes the voltage at the electrodes to vary. When the device expands or contracts in one dimension (the thickness or longitudinal direction) it generally contracts or expands respectively, in dimensions in a plane perpendicular thereto (planar or transverse directions). A piezoelectric or other force-to-signal transducing element can be utilized in the sensing transducers 128, 130, 132, 134 to produce a signal to the microcontroller 98 relating the tension in a binding of one of the attaching elements 90, 92, 94, and 96 and any change in tension produced by changes in the size and density of the muscles, or relative movement of the limb and bracing element 84.

Figure 5A:
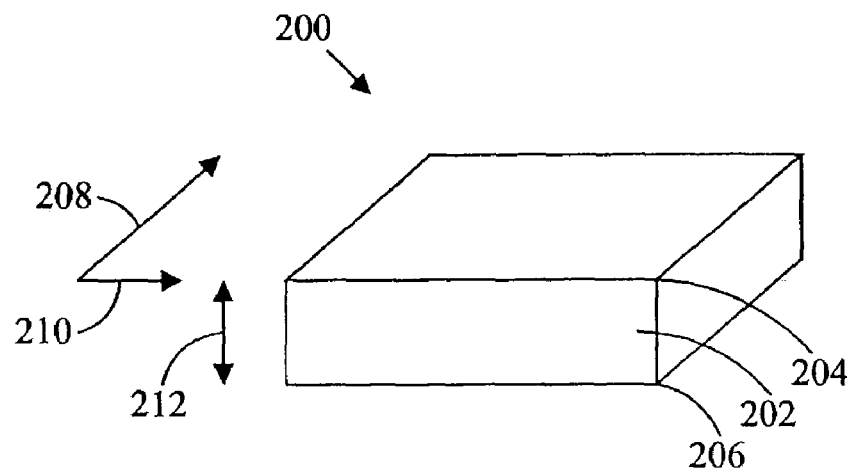
FIG. 5A is an upper front perspective view of an electroactive polymer transducer.
Figure 5B:
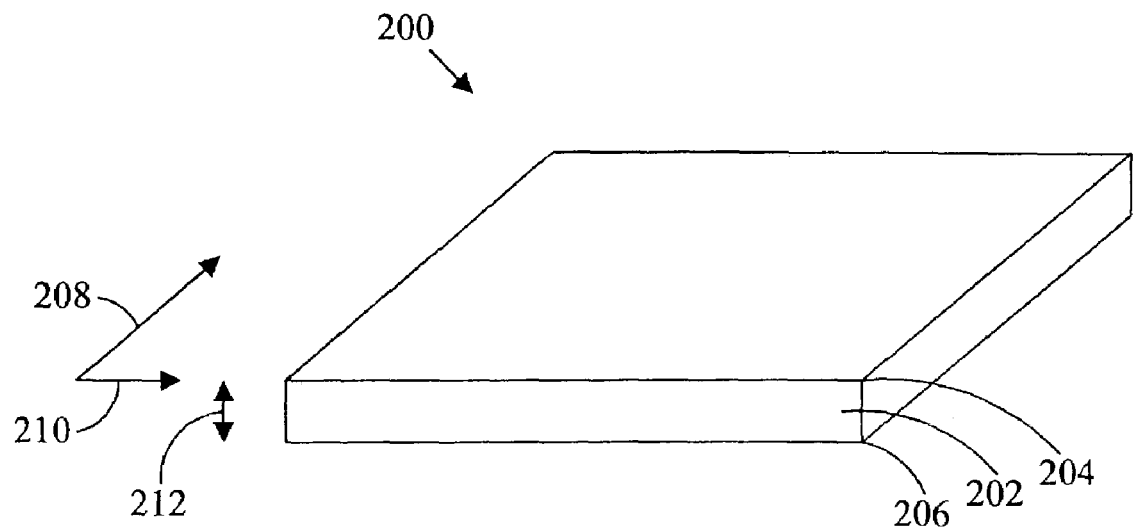
FIG. 5B is an upper front perspective view of the electroactive polymer transducer of FIG. 5A in an actuated state.

The tension in one of the bindings of the attaching elements 90, 92, 94, and 96 of the brace 80 can be varied in response to a signal output by the controller 98 to one of the drivers. Referring again to FIG. 4, a loading transducer 156 comprising plurality of electroactive polymer tensioning elements 172 is utilized to alter the length of the binding 152 and, as a consequence, the force exerted by the attaching element 150. Electroactive polymers deflect when actuated by electrical energy. To help illustrate the performance of an electroactive polymer in converting electrical energy to mechanical energy, FIG. 5A illustrates a top perspective view of a transducer portion 200 comprising an electroactive polymer 202 for converting electrical energy to mechanical energy or vice versa. An electroactive polymer refers to a polymer that acts as an insulating dielectric between two electrodes and deflects upon application of a voltage difference between the two electrodes. Top and bottom electrodes 204 and 206 are attached to the electroactive polymer 202 on its top and bottom surfaces, respectively, to provide a voltage difference across a portion of the polymer. The polymer 202 deflects with a change in electric field provided by the top and bottom electrodes 204 and 206. Deflection of the transducer portion 202 in response to a change in the electric field is referred to as actuation. As the polymer 202 changes in size, the deflection may be used to produce mechanical work. In general, deflection refers to any displacement, expansion, contraction, torsion, linear or area strain, or any other deformation of a portion of the polymer. The change in the electric field corresponding to the voltage difference applied to or by the electrodes 204 and 206 produces mechanical pressure within the polymer 202. As illustrated by comparing the length 212, width 210, and depth 208 dimensions of FIGS. 5A and 5B electroactive polymer transducers deflect in all dimensions simultaneously. In general, the transducer portion 200 continues to deflect until mechanical forces balance the electrostatic forces driving the deflection. The mechanical forces include elastic restoring forces of the polymer material, the compliance of the electrodes 204 and 206, and any external resistance provided by a device or load coupled to the transducer element.

Electroactive polymers and electroactive polymer transducers are not limited to any particular shape, geometry, or type of deflection. For example, a polymer and associated electrodes may be formed into any geometry or shape including tubes and rolls, stretched polymers attached between multiple rigid structures, and stretched polymers attached across a frame of any geometry, including curved or complex geometries; or a frame having one or more joints. Deflection of electroactive polymer transducers includes linear expansion and compression in one or more directions, bending, and axial deflection when the polymer is rolled.

Materials suitable for use as an electroactive polymer may include any substantially insulating polymer or rubber (or combination thereof) that deforms in response to an electrostatic force or whose deformation results in a change in electric field. One suitable material is NuSil CF19-2186 as provided by NuSil Technology of Carpenteria, Calif. Other exemplary materials include silicone elastomers such as those provided by Dow Corning of Midland, Mich., acrylic elastomers such as VHB 4910 acrylic elastomer as produced by 3M Corporation of St. Paul, Minn., polyurethanes, thermoplastic elastomers, copolymers comprising PVDF, pressure-sensitive adhesives, fluoroelastomers, polymers comprising silicone and acrylic moieties, and the like. Polymers comprising silicone and acrylic moieties may include copolymers comprising silicone and acrylic moieties, polymer blends comprising a silicone elastomer and an acrylic elastomer, for example. Combinations of some of these materials may also be used as the electroactive polymer in transducers.

Electronic drivers, such as the drivers 112 and 118, are typically connected to the electrodes of an electroactive polymer transducer. The voltage applied to an electroactive polymer will depend upon specifics of an application. For example a transducer may be driven electrically by modulating an applied voltage about a DC bias voltage. Modulation about a bias voltage improves sensitivity and linearity of the transducer to the applied voltage.

The deflection of an electroactive polymer can be used in a variety of ways to produce mechanical energy. Generally speaking, electroactive polymer actuators include extenders, bending beams, stacks, and diaphragms. In the binding 152 of the adjustable brace, the linear extension or contraction of the electroactive polymer in response to voltage from a driver is used to increase or decrease the tension in binding. The controller 98 can vary the tension in a binding of one or more of the attaching elements to respond to changing tension in the binding due to muscle contraction and expansion, muscle density, limb position, or another treatment variable captured in a program instruction that is executed by the microcontroller 100.

An electroactive polymer can also be used as a sensing transducer for the binding 152 of the brace attaching element 150. As the electroactive polymer 202 of a transducer is deflected the voltage at the electrodes 204 and 206 changes. The electroactive polymer sensing transducer element 174 is attached to the fabric of the binding 152 so that the transducing element is stretched or compressed by the changing tension in the binding. The voltage at the electrodes of the transducer element 174 can be used to signal a binding tension brace parameter to the controller 98.

Figure 6:
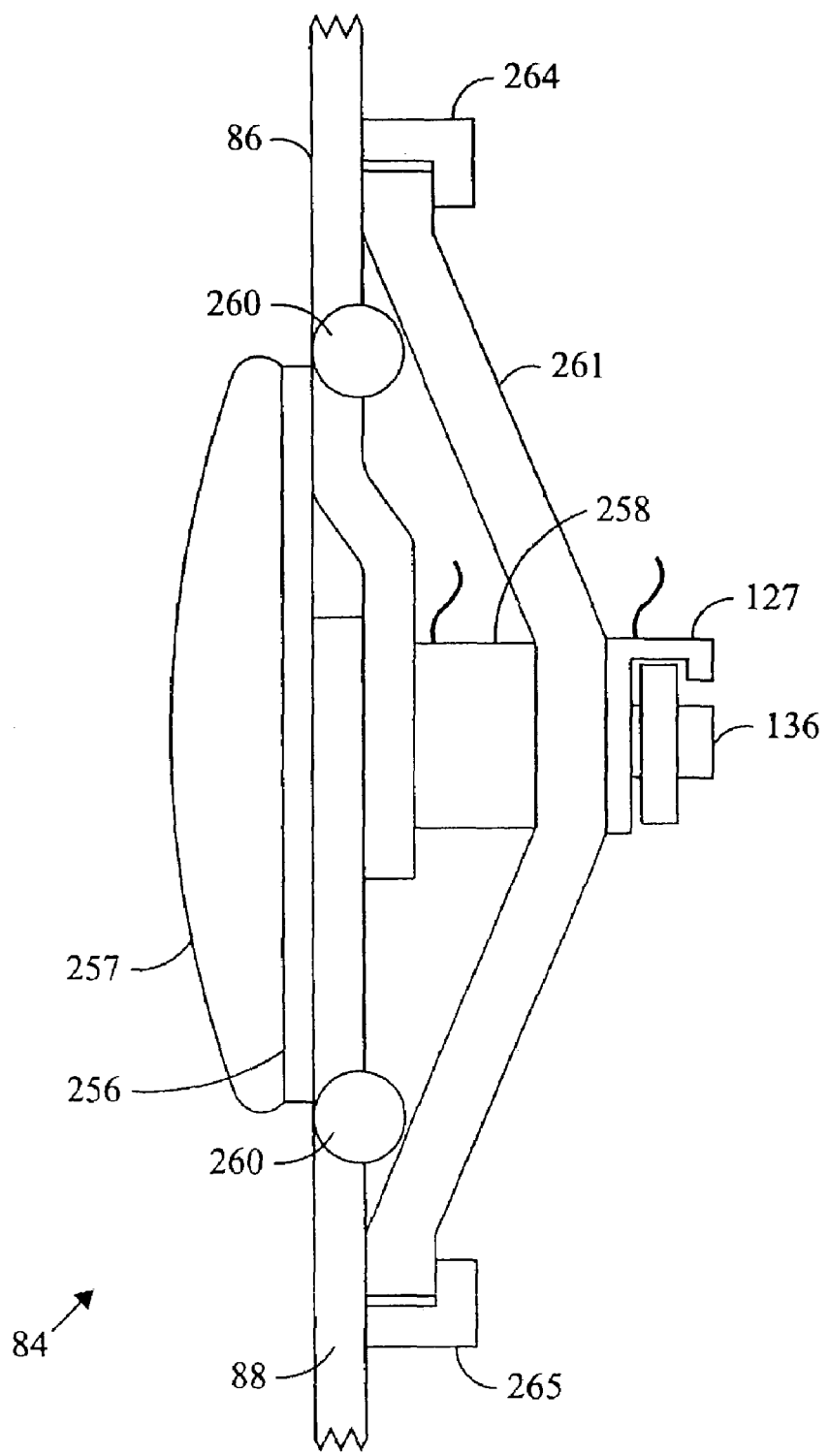
FIG. 6 is a front view of a hinge portion of an orthotic bracing element.

The adjustable brace 80 includes provisions for bending the bracing element 84 in a direction generally orthogonal to the limb to adjust the fit of the bracing element to a user's limb and to alter the compartmental loading of the braced joint. Referring to FIG. 6, the upper 86 and lower 88 levers of the bracing element 84 are connected by a hinge pin 136 facilitating relative rotation of the levers about the pin. A disk 256 attached to the hinge pin 136 on the limb side of the bracing element 84 protects the limb from the moving components of the bracing element and may be used to compress a condyle pad 257 providing lateral stability to the joint. The hinge pin 136 passes through a central aperture in a loading transducer 258 retaining the transducer in rotational engagement with the proximal end to the upper lever 86. A loading disk 261 with an offset central portion abuts an end of the loading transducer 258 and is restrained to the upper 86 and lower 88 levers by sliding blocks 264 and 265 welded to the levers and engaging the loading disk. When the length of the transducer 258 changes, the distal ends of the upper 86 and lower 88 levers are deflected in the direction of the axis of the hinge pin 136 or substantially normal to the limb. The upper 86 and lower 88 levers may include transverse hinges 260 to reduce the force necessary to deflect the levers. The loading transducer 258 illustrated in FIG. 6 is a piezoelectric or electro-active polymer transducer having a length that is variable in response to a voltage applied by a driver 116 that is controlled by the controller 98. The lateral profile of the bracing element can be varied to conform to the user's limb and alter the compartmental loading of the joint. In addition, the brace 80 includes one or more sensing transducers 138, such as a strain gauge to sense the stress in, and result from, the displacement of a lever of the bracing element 84. The sensing transducer 138 provides an input signal and feedback to the controller 98 related to the displacement of the levers 86 and 88 by the loading transducer or as a result of external loading. If a prescribed level of displacement or stress is sensed indicating a lateral blow to the limb, the controller 98 can cause the loading transducer 258 to deflect the bracing element to aid in resisting displacement of the brace that might injure the joint.

A shaft encoder 127 is also attached to the hinge pin to sense changes in the relative angular positions of the upper 86 and lower 88 levers. The controller 98 can vary the force exerted by the attaching elements, the lateral deflection of the brace, or the assistance or resistance of the brace to joint flexing as a function of the angular position of the levers and, therefore, the limb elements. For example, the force exerted by the tensioning structures might be reduced when the foot is raised and the tibia is not in position to apply an injurious load to the joint.

The adjustable brace 80 also includes a loading transducer to vary the force required for relative rotation of the upper 86 and lower 84 levers about the hinge 136. As illustrated in FIG. 3, an electroactive polymer filament 140 is used to assist joint extension or resist flexion in a first direction. A second electroactive polymer filament 141 received on the opposite side of the bracing element joint can apply extension and flexion forces opposing those of the first filament 140. The electroactive polymer filament 140 is anchored to the upper 86 and lower 88 levers and passes over a leveraging sheave 142 at the hinge 136. Voltage applied to electrodes of the electroactive polymer filament 140 by the driver 114 in response to signals from the controller 98 causes the length of the filament to change assisting extension or resisting flexion of the joint as desired for a specific treatment regimen. The loading transducer 140 may also be used to assist flexion and resist extension by routing the filament on the opposite side of the sheave 142.

Figure 7:
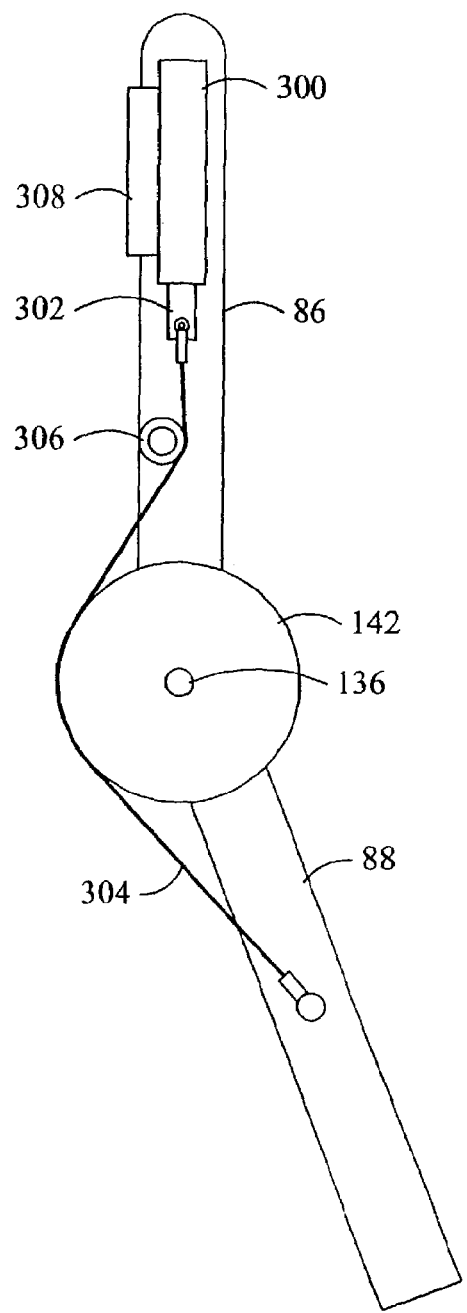
FIG. 7 is a side view of a bracing element of an orthotic brace and a loading transducer arranged to effect rotation of the levers of the bracing element.

Referring the FIG. 7, a linear actuator 300 can also be used to in assisting or resisting joint flexing. A piston rod 302 of the linear actuator 300, attached to the upper lever 86, is attached to the lower lever 88 of the bracing element 84 by a filament 304. The filament 304 passes over a sheave 142 at the hinge 136 and an idler 306 that reduces side loading of the piston rod 302. The linear actuator 300 may be a pneumatic or hydraulic actuator having a valve 308 with flow characteristics controllable by the controller 98. By controlling the flow into and out of the linear actuator 300 the force required to displace the piston rod 302 can be varied. The controller 98 can vary the force exerted by the actuator 300 as a function of the angular position of the levers 86 and 88 as sensed by the shaft encoder 127. If a source of pressurized fluid is provided, the actuator 300 can serve as a motor generating a force assisting extension of the joint (or assisting joint flexion by reversing the position of the filament 304 on the sheave 142).

Figure 9:
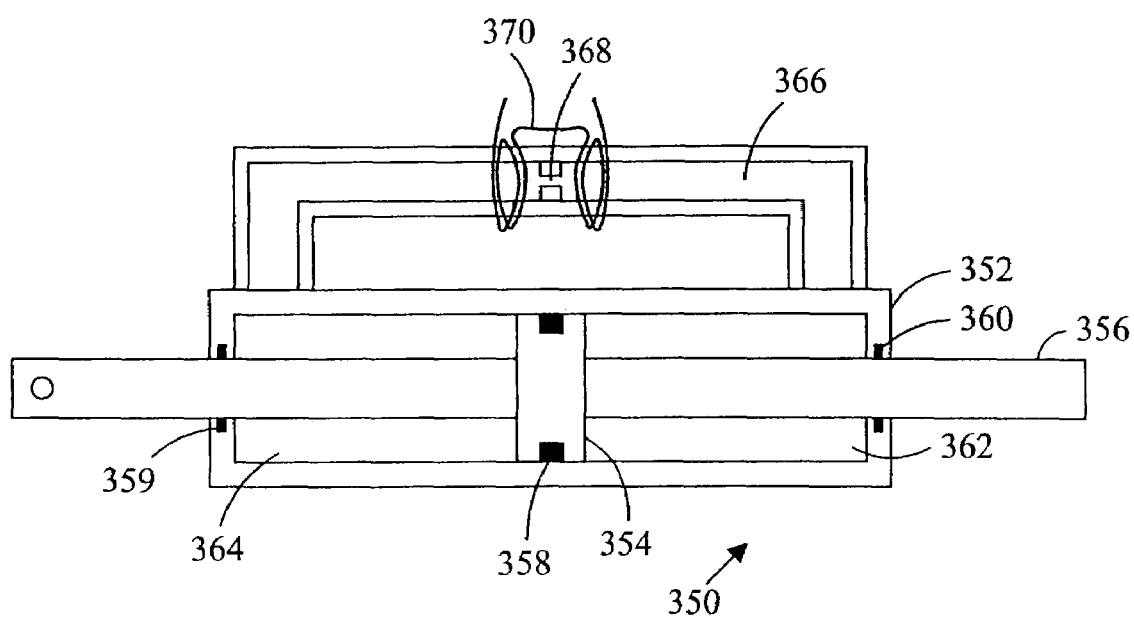
FIG. 9 is a sectional schematic of a magneto-rheological linear transducer.

An alternative linear loading transducer 300 incorporating a magneto-rheological fluid can be utilized to provide variable resistance under the control of the controller 98. FIG. 9 illustrates a linear loading transducer comprising a non-differential linear actuator 350 that includes a shell 352 and a movable piston 354 connected to a piston rod 356. Seals 358, 359, and 360 seal fluid chambers 362 and 364 on opposing sides of the piston 354. The fluid chambers 362 and 364 are connected by a suitable fluid passage 366. An orifice 368 limits the flow rate in the fluid passage 366. The resistance to flow created by the orifice 368 is determined by the size of the orifice and the viscosity of the fluid flowing through the orifice. A magneto-rheological fluid comprises generally a carrier, such as water, oil, or silicone, and suspended particles of magnetic material, known as carbonyl iron. The viscosity of a magneto-rheological fluid can be varied by altering the strength of a magnetic field applied to the fluid. In the actuator 350, the voltage in a coil 370 adjacent to the orifice 368 is controlled by the controller 98 to regulate the viscosity of the magneto-rheological fluid that is transferred from one fluid chamber 362 to the other 364 by the piston's displacement. When the lever 88 is rotated, the filament 304 attached to the lever and the piston rod 356 causes the piston 354 to be displaced in the shell 352.

Figure 8:
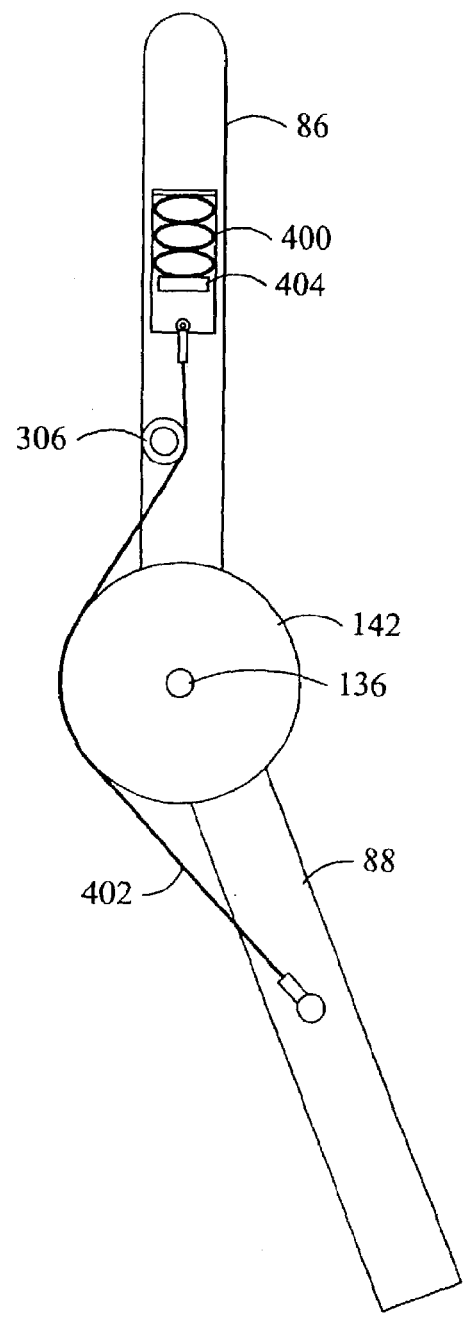
FIG. 8 is a side view of a bracing element of an orthotic brace and an alternative loading transducer arranged to effect rotation of the levers of the bracing element.

Alternatively, a piezoelectric flextensional transducer or an electroactive polymer transducer 400 may be applied as illustrated in FIG. 8. A typical piezoelectric unimorph comprises a single piezoelectric element externally bonded to a flexible metal foil which is stimulated by the piezoelectric element when activated with a changing voltage. This produces axial buckling or deflection as foil opposes the movement of the piezoelectric element. The actuator movement for a unimorph can be either contraction or expansion. A piezoelectric bimorph device includes an intermediate flexible metal foil sandwiched between two piezoelectric elements bonded to a plate. Electrodes are bonded to each of the major surfaces of the ceramic elements and the metal foil is bonded to the inner two electrodes. A multilayer device known as a multimorph can be made by stacking alternating layers of ceramic elements and metal plates. When a voltage is applied to the electrodes, the bimorph or multimorph bends. Bimorphs and multimorphs exhibit more displacement than unimorphs because under the applied voltage, one ceramic element will contract while the other expands. Deflection of the electroactive polymer transducer or the piezoelectric unimorph, bimorph or multimorph transducer 400 linked by the filament 402 to the lever 88 and anchored 404 to the lever 86 can be used to exert force to resist or assist flexing to the levers of the bracing elements.

Figure 11:
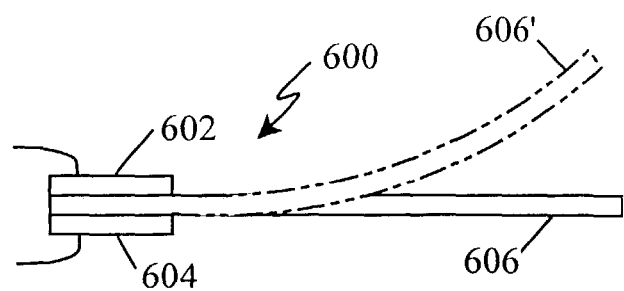
FIG. 11 is a side elevation of a polymer-metal composite transducer.
Figure 12:
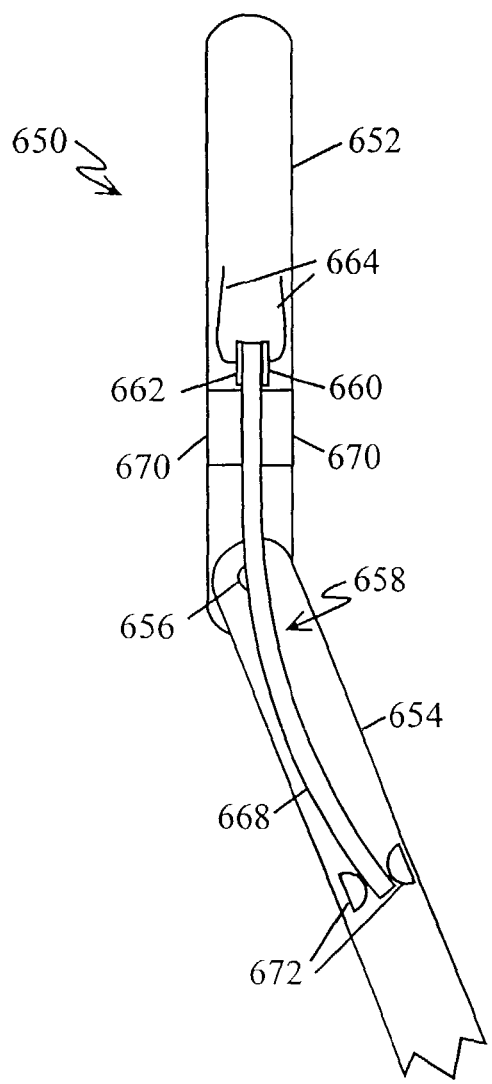
FIG. 12 is a side view of a bracing element of an orthotic brace and including a polymer-metal composite loading transducer arranged to effect rotation of the levers of the bracing element.

The contractile and sensing transducers of the adjustable orthotic brace may comprise polymer-metal composite actuators and sensors. An ionic polymer-metal composite (IPMC) comprises a polymer having ion exchanging capability that is first chemically treated with an ionic salt solution of a conductive medium, such as a metal, and then chemically reduced. An ion exchange polymer refers to a polymer designed to selectively exchange ions of a single charge with its on incipient ions. Ion exchange polymers are typically polymers of fixed covalent ionic groups, such as perfluorinated alkenes, styrene-based, or divinylbenzene-based polymers. Referring to FIG. 11, a simple polymer-metal composite acutator or sensor 600 comprises suitable electrodes 602, 604 attached to a polymer-metal composite element. When a time varying electric field is applied to the electrodes 602, 604 attached a polymer-metal composite element 606, the element will exhibit a large dynamic deformation 606'. Referring to FIG. 12, an embodiment of an adjustable orthotic brace comprises a bracing element 650 including upper 652 and lower 654 levers joined with a pivot 656 at their distal ends. A polymer-metal composite transducer 658 is used to control the force required for relative rotation of the upper 652 and lower 654 levers or to sense the rotational displacement of the levers. A voltage applied to the electrodes 660, 662 of the transducer 658 through wires 664 causes the polymer-metal composite element 668, which is restrained to the brace levers 652, 654 by mounting blocks 670, 672, respectively, to deflect. The deflection of the polymer-metal composite element 668 can be used to either aid or resist rotation of the levers 652, 654 according to a treatment regimen.

On the other hand, when such a polymer-metal composite element 606 undergoes dynamic deformation, a dynamic electric field is produced across the electrodes 602, 604 attached to the composite element. If the voltage at the electrodes 660, 662 of the transducer 658 is measured when the polymer-metal composite element 668 is deflected, the force being exerted on the levers 652, 654 can be measured.

Feedback to the controller 98 is provided by a sensing transducer 144 such as a strain gage at the attachment of a loading transducer or the filament 140 to a lever 86 or 88 of the bracing element 84. The controller 98 can vary the force exerted by the loading transducer 140 throughout the range of motion of the joint by executing program instructions relating the position of the levers as sensed by the shaft encoder 127 and the force generated by the loading transducer as determined by the sensing transducer 142.

Figure 10:
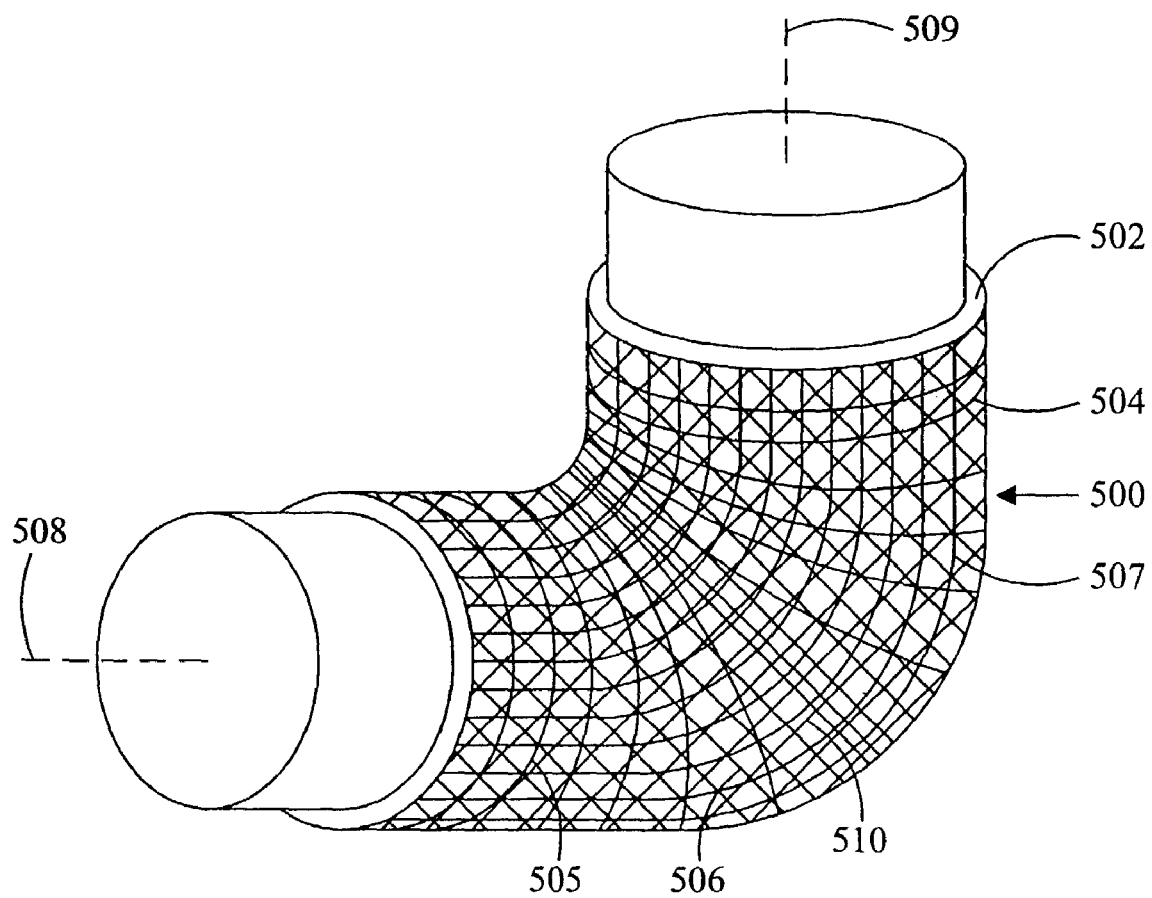
FIG. 10 is a perspective view of an adjustable orthotic sleeve brace.

Another embodiment of an adjustable brace comprises an elastic sleeve incorporating loading and sensing transducers. A sleeve is an expandable, slip-on device that typically comprises nylon-covered neoprene. While sleeves are simple, easy to fit, and relatively inexpensive, a simple sleeve cannot apply leverage to the joint which is necessary for ligamentous support and lessening the likelihood of joint injury. Referring to FIG. 10, the adjustable orthotic elbow sleeve 500 comprises an insulating neoprene shell 502 confining portions of the upper arm, the lower arm, and the elbow. The shell 502 compresses the soft tissue of the arm and elbow and keeps the joint warm. A covering for the shell 502 comprises a mesh 504 of interconnected electroactive polymer filaments 506. A first plurality of electroactive polymer filaments is arranged circumferentially around the sleeve 505 and a second plurality of filaments is aligned generally longitudinally 507. A third plurality of filaments 506 are arranged on a bias to the axes of the limb elements 508 and 509 and a fourth plurality of the filaments 510 are arranged at second bias to the axis of the limb elements and at a bias to the fibers of the third plurality. The lengths of the electroactive polymer filaments 506 are responsive to a voltage applied to electrodes on the surfaces of the filaments by a driver controlled by a controller 98. As the lengths of the circumferential filaments 505 are changed, the sleeve is tightened and loosen on the limb and as the lengths of the longitudinal filaments of the second plurality are changed force can be applied to assist or resist flexion and extension of the joint. As the length of a biased filament changes, the connected neighboring filaments are either tightened and pulled together or loosened and allowed to separate. Increasing the tensioning of the filaments 506 tightens the sleeve 500 on the arm and since the filaments are arranged on a bias, the sleeve can support the muscles and ligaments of the joint in resisting rotation of the limb elements and articulation of the elbow.

While the exemplary braces 80 and 500 are appropriate for application to the knee and elbow, respectively, the adjustable bracing system may be applied to many of the body's joints. For example, a back brace adjustable to accommodate motions specific to the vertebrae may be used for injury protection, rehabilitation, and strength augmentation of the lumbar and thoracic vertebrae. Likewise, the adjustable orthotic brace system can be applied to the hand, finger, wrist, shoulder, and hip. For example, a partial shirt having a sleeve extending over the proximal humerus and encircling the upper torso or the shoulder from the supraclavicular region to the axilla and constructed of neoprene and an electroactive mesh may be used to treat the shoulder. Similarly, a glove or individual finger sleeve including an electroactive mesh can be used to adjustably brace the joints of the fingers and hand. The adjustable brace system may also be applied to foot and ankle braces and built into a shoe to prevent foot or ankle injury or to aide in strengthening or rehabilitation of a foot or an ankle.

The adjustable brace facilitates a method of supporting a joint that is useful in protecting the joint from injury and in treating injury and deformity through physical therapy and strength augmentation. The joint is supported by binding the levers 86 and 88 of the bracing element 84 to elements of the limb on each side of the joint and altering a characteristic of the bracing element 84 or one of the bindings in response to a requirement of a treatment regimen or a sensed bracing parameter resulting from the joint's movement. The force binding the limb to the bracing element 84 can be varied to adjust the brace for changes in the dimensions and density of muscles during joint operation or to vary the compartmental loading of the joint. The shape of the brace can be altered to vary the compartmental loading and to treat certain joint conditions. In addition, a force can be applied to resist or assist articulation of the joint to either strengthen the muscles of the limb or aid limb function with weakened muscles.

Figure 13:
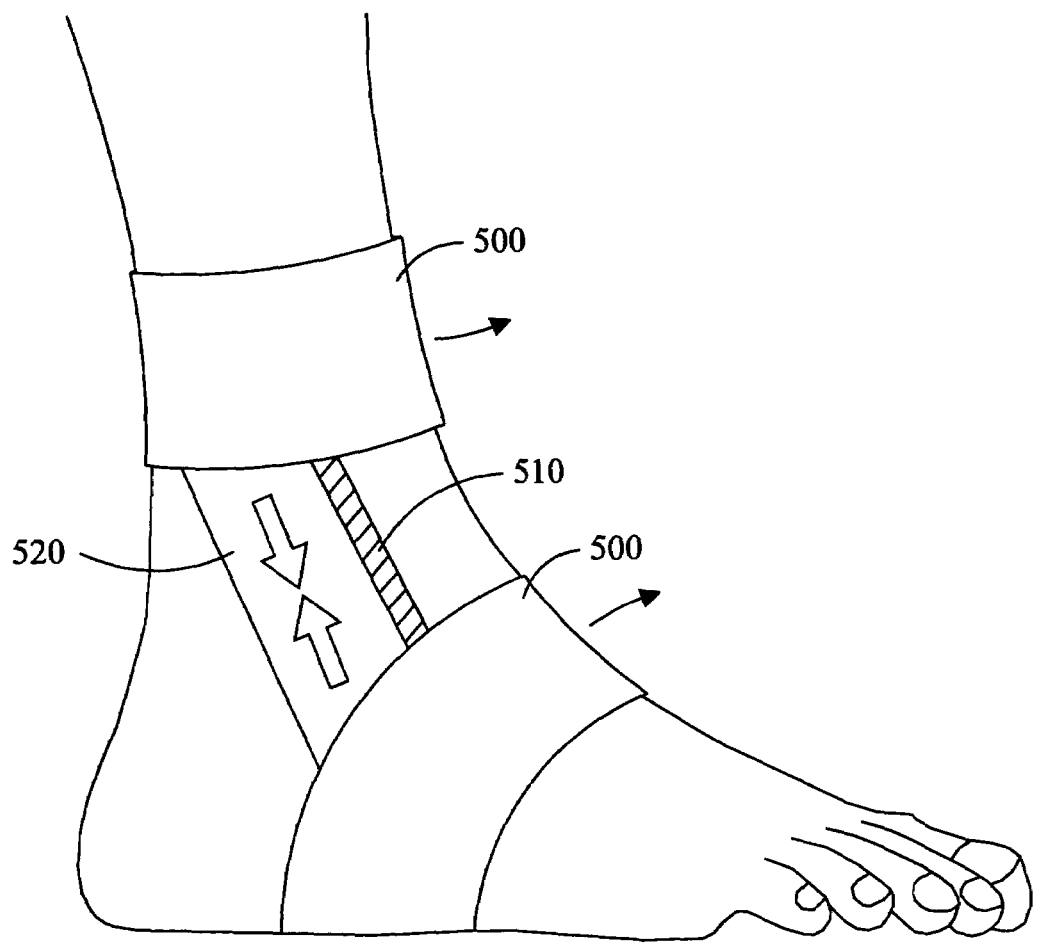
FIG. 13 is a side view of a shoe based bracing system.

Referring to FIG. 13, a circumferential band 500 at least partially surrounding the leg or ankle of the user constricts to bind the shoe to the leg/ankle/foot when a sufficient force threatens to potentially injure the ankle. To detect this force strain detecting devices 510, such as strain gages, may be located within the shoe. One or more dynamic materials 520 may likewise be located within the shoe to provide a counteracting force(s) to the detected force. For example, the dynamic material 520 may be an electroactive polymer that stabilizes the ankle, such as by applying counteracting forces. While one or more of these materials are supported within the shoe of the user, all of the aforementioned embodiments may likewise be included. The bands 500 may be detachably attachable to the leg/ankle/foot and/or the shoe, as desired. In addition, these features may likewise be incorporated in a sleeve that fits over the foot and/or ankle.

The detailed description, above, sets forth numerous specific details to provide a thorough understanding of the present invention. However, those skilled in the art will appreciate that the present invention may be practiced without these specific details. In other instances, well known methods, procedures, components, and circuitry have not been described in detail to avoid obscuring the present invention.

All the references cited herein are incorporated by reference.

The terms and expressions that have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims that follow.

The invention claimed is:

1. An adjustable orthotic bracing system comprising:
   (a) a bracing element including a first lever hinged to a second lever;
   (b) an attaching element restraining said bracing element to a limb;
   (c) a loading transducer altering at least one of said bracing element and said attaching element in response to a first signal;
   (d) a program for a data processing device including a program instruction;
   (e) a data processing device outputting said first signal to said loading transducer in response to said program instruction;
   (f) wherein said attaching element comprises a binding having a length arranged to confine said bracing element and said limb; and
   (g) wherein said loading transducer is arranged to alter said length of said binding in response to said first signal.

2. The system of claim 1 wherein said loading transducer comprises an electroactive polymer.

3. An adjustable orthotic bracing system comprising:
   (a) a bracing element including a first lever hinged to a second lever;
   (b) an attaching element restraining said bracing element to a limb;
   (c) a loading transducer altering at least one of said bracing element and said attaching element in response to a first signal;
   (d) a program for a data processing device including a program instruction;
   (e) a data processing device outputting said first signal to said loading transducer in response to said program instruction;
   (f) wherein said attaching element comprises a binding having a length arranged to confine said bracing element and said limb;
   (g) wherein said loading transducer comprises a link connecting a portion of said binding to one of another portion of said binding and said bracing element, said link having a length responsive to said first signal; and
   (h) wherein said link comprises a piezoelectric actuator.

4. An adjustable orthotic bracing system comprising:
   (a) a bracing element including a first lever hinged to a second lever;
   (b) an attaching element restraining said bracing element to a limb;
   (c) a loading transducer altering at least one of said bracing element and said attaching element in response to a first signal;
   (d) a program for a data processing device including a program instruction;
   (e) a data processing device outputting said first signal to said loading transducer in response to said program instruction; and
   (f) wherein said loading transducer altering at least one of said bracing element and said attaching element in response to a first signal comprises a transducer arranged to deflect a portion of said bracing element in a direction substantially normal to said limb in response to said first signal.

5. The system of claim 4 wherein said transducer includes a piezoelectric actuator.

6. An adjustable orthotic bracing system comprising:
   (a) a bracing element including a first lever hinged to a second lever;
   (b) an attaching element restraining said bracing element to a limb;
   (c) a loading transducer altering at least one of said bracing element and said attaching element in response to a first signal;
   (d) a program for a data processing device including a program instruction;
   (e) a data processing device outputting said first signal to said loading transducer in response to said program instruction;
   (f) wherein said loading transducer altering at least one of said bracing element and said attaching element in response to a first signal comprises a transducer arranged for substantially rotating said first lever and said hinged second lever of said bracing element; and
   (g) wherein said transducer comprises an electroactive polymer connected to said first and said second levers and having a dimension alterable in response to said first signal.

7. An adjustable orthotic bracing system comprising:
   (a) a bracing element including a first lever hinged to a second lever;
   (b) an attaching element restraining said bracing element to a limb;
   (c) a loading transducer altering at least one of said bracing element and said attaching element in response to a first signal;
   (d) a program for a data processing device including a program instruction;
   (e) a data processing device outputting said first signal to said loading transducer in response to said program instruction;
   (f) wherein said loading transducer altering at least one of said bracing element and said attaching element in response to a first signal comprises a transducer arranged for substantially rotating said first lever and said hinged second lever of said bracing element; and
   (g) wherein said transducer comprises a piezoelectric actuator connected to said first and said second levers.

8. An adjustable orthotic bracing system comprising:
   (a) a bracing element including a first lever hinged to a second lever;
   (b) an attaching element restraining said bracing element to a limb;
   (c) a loading transducer altering at least one of said bracing element and said attaching element in response to a first signal;
   (d) a program for a data processing device including a program instruction;
   (e) a data processing device outputting said first signal to said loading transducer in response to said program instruction;
   (f) a sensing transducer outputting a second signal to said data processing device, said sensing transducer being responsive to a condition of at least one of said bracing element and said attaching element;
   (g) a program instruction relating said second signal and said first signal;

(h) wherein said sensing transducer is arranged to output said second signal in response to a change in a tension in said binding; and
(i) wherein said sensing transducer comprises an electroactive polymer.

9. An adjustable orthotic bracing system comprising:
(a) a bracing element including a first lever hinged to a second lever;
(b) an attaching element restraining said bracing element to a limb;
(c) a loading transducer altering at least one of said bracing element and said attaching element in response to a first signal;
(d) a program for a data processing device including a program instruction; and
(e) a data processing device outputting said first signal to said loading transducer in response to said program instruction;
(f) a sensing transducer outputting a second signal to said data processing device, said sensing transducer being responsive to a condition of at least one of said bracing element and said attaching element;
(g) a program instruction relating said second signal and said first signal;
(h) wherein said sensing transducer is arranged to output said second signal in response to a change in a tension in said binding;
(i) wherein said sensing transducer comprises a link connecting a portion of said binding to one of another portion of said binding and said bracing element, said link producing said second signal in response to a change in said tension; and
(j) wherein said link comprises a piezoelectric transducer.

10. An adjustable orthotic bracing system comprising:
(a) a bracing element including a first lever hinged to a second lever;
(b) an attaching element restraining said bracing element to a limb;
(c) a loading transducer altering at least one of said bracing element and said attaching element in response to a first signal;
(d) a program for a data processing device including a program instruction; and
(e) a data processing device outputting said first signal to said loading transducer in response to said program instruction;
(f) a sensing transducer outputting a second signal to said data processing device, said sensing transducer being responsive to a condition of at least one of said bracing element and said attaching element;
(g) a program instruction relating said second signal and said first signal;
(h) wherein said sensing transducer outputting a second signal responsive to a condition of at least one of said bracing element and said attaching element comprises a transducer arranged to output a signal in response to a rotation of said first lever relative to said second lever; and
(i) wherein said transducer comprises an electroactive polymer having an electrical characteristic responsive to a change in a dimension, said electroactive polymer being connected to said first and said second levers such that relative rotation of said first and said second levers will change said dimension.

11. An adjustable orthotic brace comprising:
(a) a first lever having a distal end and a proximal end;
(b) a second lever having a distal end and a proximal end, said proximal end and said proximal end of said first lever hinged for substantially relative rotation of said levers;
(c) a first attaching element restraining said first lever to a first element of a limb;
(d) a second attaching element restraining said second lever to said second element of said limb;
(e) a loading transducer to alter a force exerted on at least one of said first element of said limb by said first attaching element and said second element of said limb by said second attaching element;
(f) wherein at least one of said attaching elements comprises a binding having a length arranged to confine at least one of said first and said second levers and said limb; and
(g) wherein said loading transducer is arranged to alter said length of said binding.

12. The apparatus of claim 11 wherein said loading transducer comprises an electroactive polymer.

13. The apparatus of claim 11 wherein said loading transducer comprises a link connecting a portion of said binding to one of another portion of said binding and said bracing element, said link having a length responsive to said first signal.

14. The apparatus of claim 13 wherein said link comprises a piezoelectric actuator.

15. An adjustable orthotic brace comprising:
(a) a first lever having a distal end and a proximal end;
(b) a second lever having a distal end and a proximal end, said proximal end and said proximal end of said first lever hinged for substantially relative rotation of said levers;
(c) a first attaching element restraining said first lever to a first element of a limb;
(d) a second attaching element restraining said second lever to said second element of said limb;
(e) a loading transducer arranged to displace said proximal end of at least one said first and said second levers relative to said distal end of said first lever and said second lever, respectively, in a direction substantially normal to said limb; and
(f) wherein said loading transducer includes a piezoelectric actuator.

16. An adjustable orthotic brace comprising:
(a) a first lever having a distal end and a proximal end;
(b) a second lever having a distal end and a proximal end, said proximal end and said proximal end of said first lever hinged for substantially relative rotation of said levers;
(c) a first attaching element restraining said first lever to a first element of a limb;
(d) a second attaching element restraining said second lever to said second element of said limb;
(e) a loading transducer arranged to displace said proximal end of at least one said first and said second levers relative to said distal end of said first lever and said second lever, respectively, in a direction substantially normal to said limb;
(f) a second loading transducer to alter a force exerted on at least one of said first element of said limb by said first attaching element and said second element of said limb by said second attaching element;
(g) wherein at least one of said attaching elements comprises a binding having a length arranged to confine at least one of said first and said second levers and said limb; and (h) wherein said loading transducer is arranged to alter said length of said binding.

17. The apparatus of claim 16 wherein said loading transducer comprises an electroactive polymer.

18. The apparatus of claim 16 wherein said second loading transducer comprises a link connecting a portion of said binding to one of another portion of said binding and said bracing element, said link having a length responsive to said first signal.

19. The apparatus of claim 18 wherein said link comprises a piezoelectric actuator.

20. An adjustable orthotic brace comprising:
   (a) a first lever having a distal end and a proximal end;
   (b) a second lever having a distal end and a proximal end, said proximal end and said proximal end of said first lever hinged for substantially relative rotation of said levers;
   (c) a first attaching element restraining said first lever to a first element of a limb;
   (d) a second attaching element restraining said second lever to said second element of said limb;
   (e) a transducer arranged for effecting substantially relative rotation of said distal ends of said first and said second levers; and
   (f) wherein said transducer comprises an electroactive polymer connected to said first and said second levers and having a dimension alterable to effect rotation of said hinged levers.

21. An adjustable orthotic brace comprising:
   (a) a first lever having a distal end and a proximal end;
   (b) a second lever having a distal end and a proximal end, said proximal end and said proximal end of said first lever hinged for substantially relative rotation of said levers;
   (c) a first attaching element restraining said first lever to a first element of a limb;
   (d) a second attaching element restraining said second lever to said second element of said limb;
   (e) a transducer arranged for effecting substantially relative rotation of said distal ends of said first and said second levers; and
   (f) wherein said transducer comprises a piezoelectric actuator connected to said first and said second levers and having dimension alterable to effect rotation of said hinged levers.

* * * * *